United States Patent [19]
Gerken et al.

[11] Patent Number: 5,538,493
[45] Date of Patent: Jul. 23, 1996

[54] CENTRIFUGATION SYSTEM WITH A ROTATABLE MULTI-ELEMENT CARRIER

[75] Inventors: Hero Gerken; Dieter Bouchain, both of Hamburg, Germany

[73] Assignee: Eppendorf-Netheler-Hinz GmbH, Hamburg, Germany

[21] Appl. No.: 166,759

[22] Filed: Dec. 14, 1993

[30] Foreign Application Priority Data

Dec. 16, 1992 [DE] Germany ................ 42 42 476.3

[51] Int. Cl.⁶ ........................................ B04B 5/02
[52] U.S. Cl. ........................................ 494/016
[58] Field of Search ............... 494/10, 16, 20, 494/21, 31, 33, 43, 85; 422/72

[56] References Cited

U.S. PATENT DOCUMENTS

| | | | |
|---|---|---|---|
| 330,779 | 11/1885 | Frederiksen et al. | 494/16 |
| 330,780 | 11/1885 | Frederiksen et al. | 494/16 |
| 2,340,825 | 2/1944 | Stern | 494/16 |
| 4,301,964 | 11/1981 | Cowell | 494/16 |
| 4,306,676 | 12/1981 | Edwards et al. | 494/16 |
| 4,586,918 | 5/1986 | Cole | 494/20 |
| 5,242,371 | 9/1993 | Sato et al. | 494/16 |

FOREIGN PATENT DOCUMENTS

| | | | |
|---|---|---|---|
| 192571 | 8/1986 | European Pat. Off. | 494/16 |
| 54-21670 | 2/1979 | Japan | 494/16 |

Primary Examiner—Charles E. Cooley
Attorney, Agent, or Firm—Anderson, Kill, Olick & Oshinsky

[57] ABSTRACT

A system for centrifugation of samples includes at least one carrier, which is provided with a plurality of elements connected with each other by joints and having each an uptake for receiving a sample to be centrifuged, and a rotor for supporting the carrier, with the elements being arranged, in a centrifuged position of the elements, along a circle having its center lying on the rotational axis of the rotor.

24 Claims, 10 Drawing Sheets

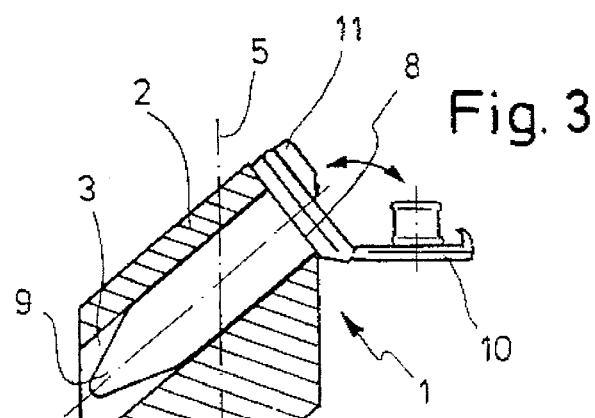
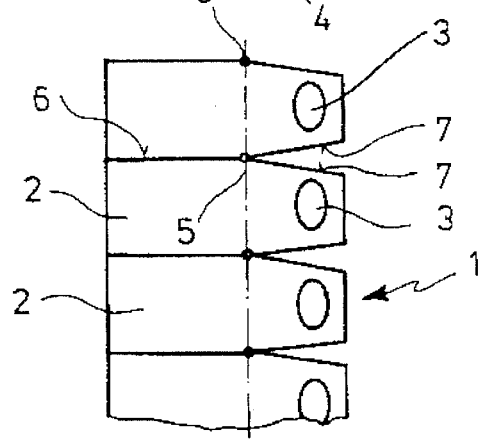
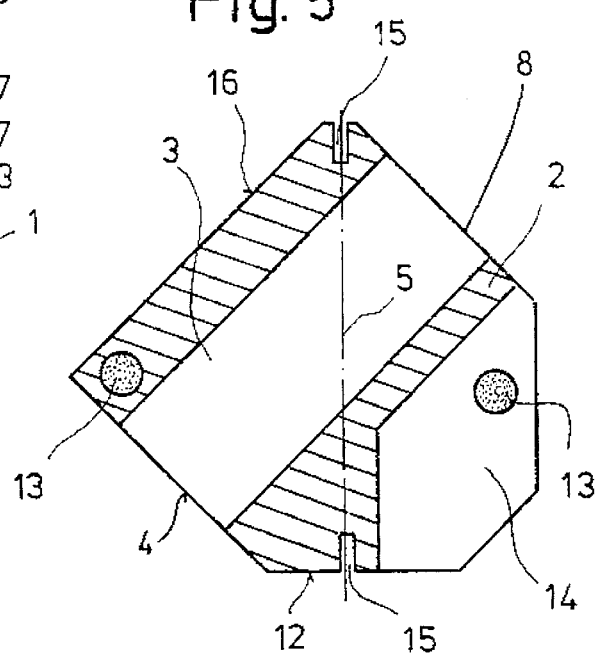
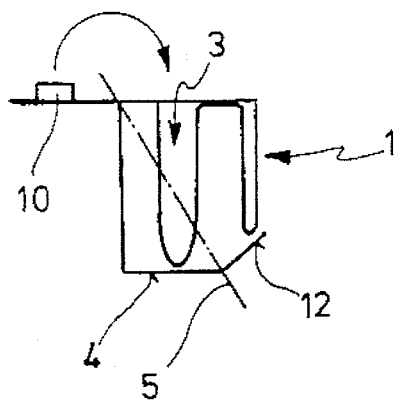
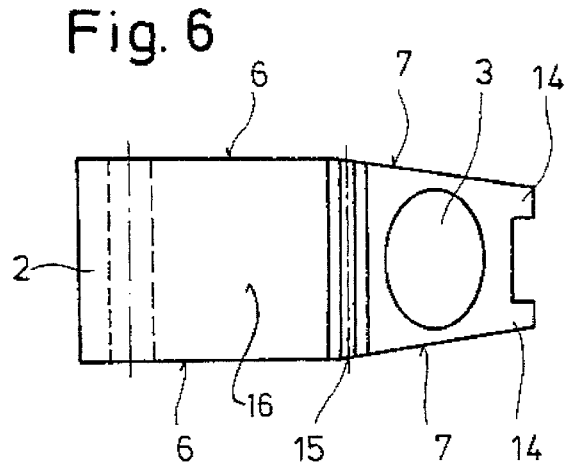

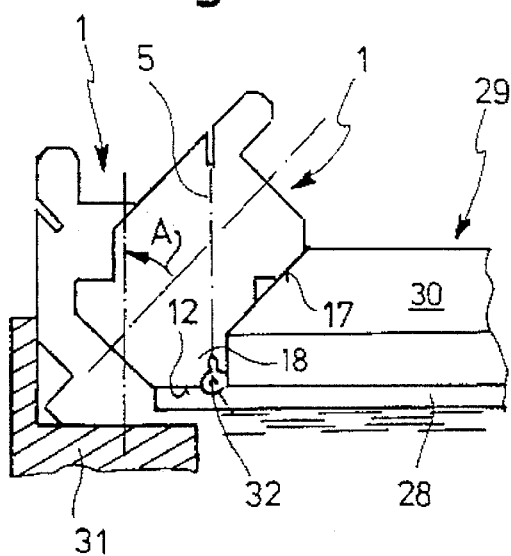
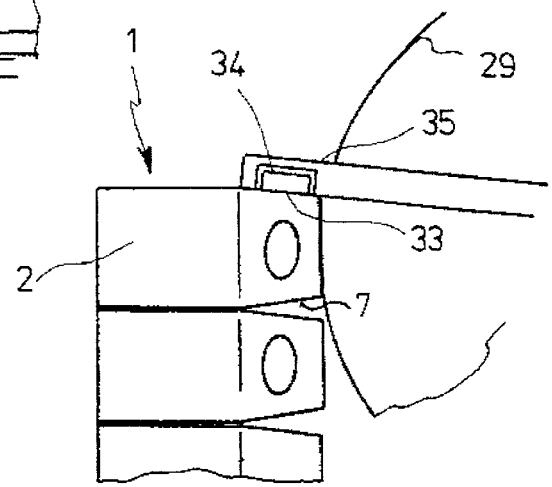
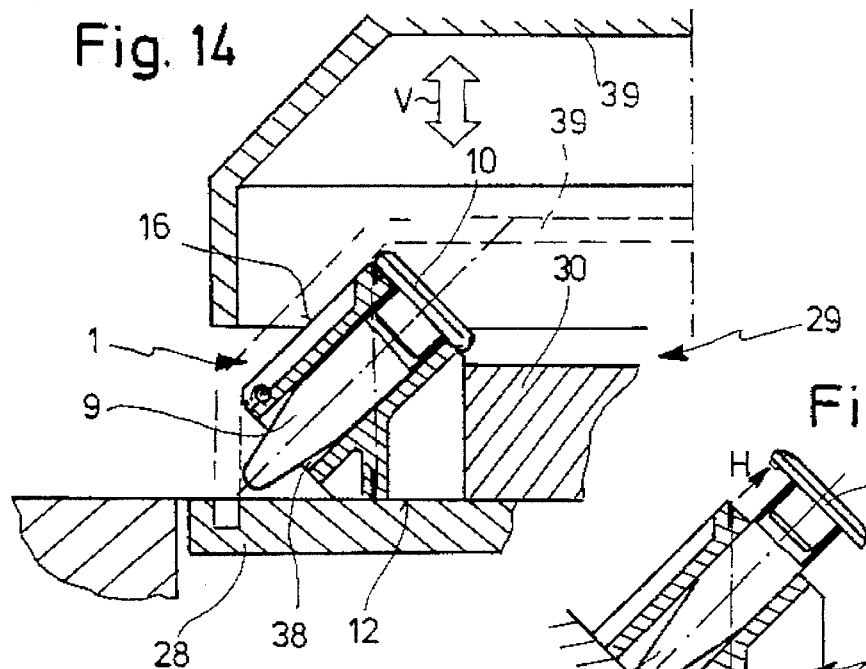
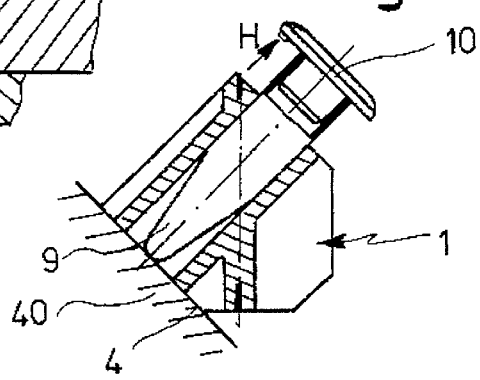

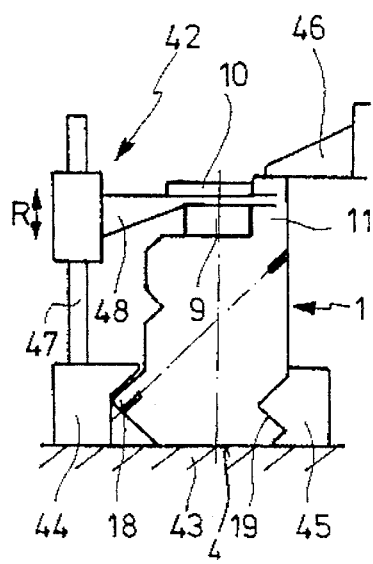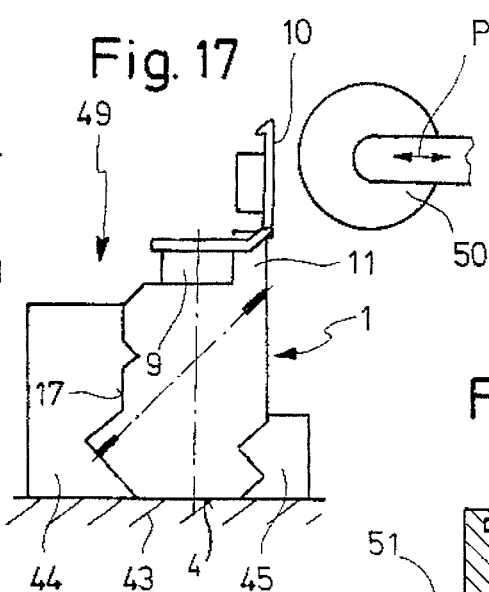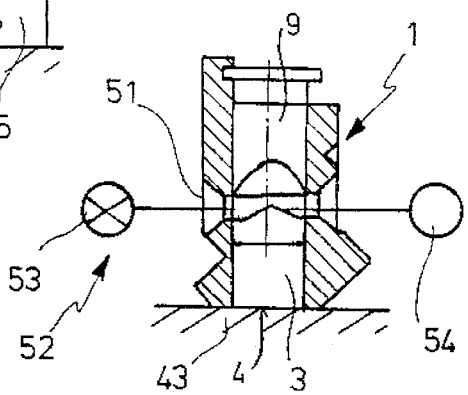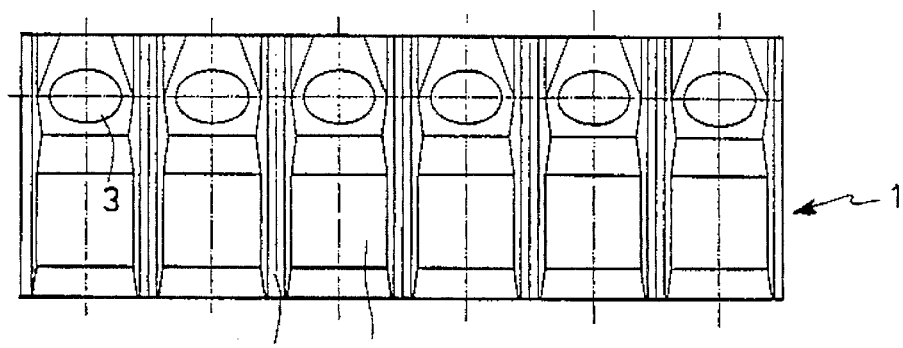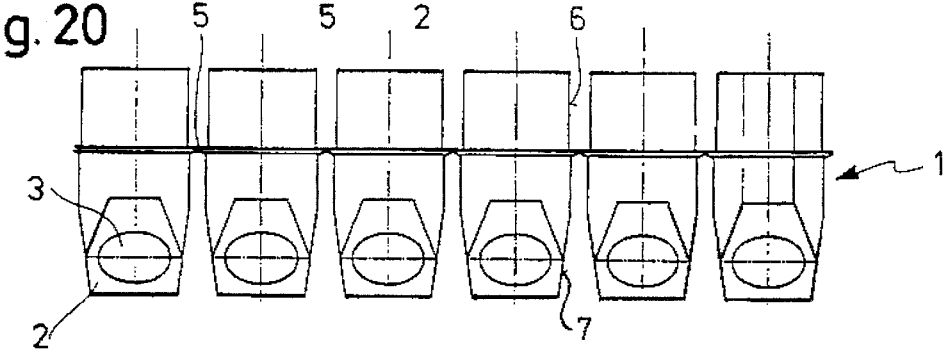

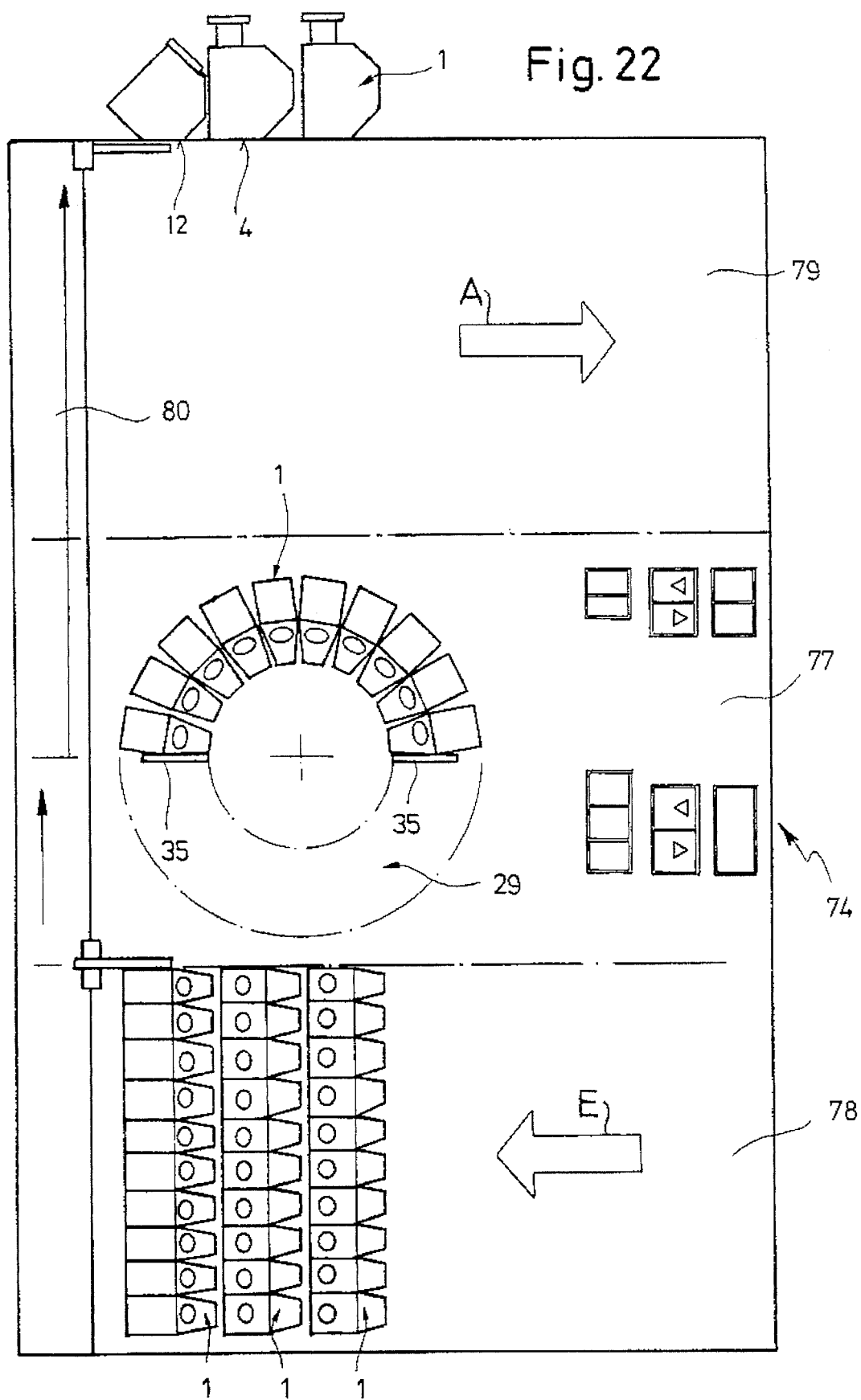

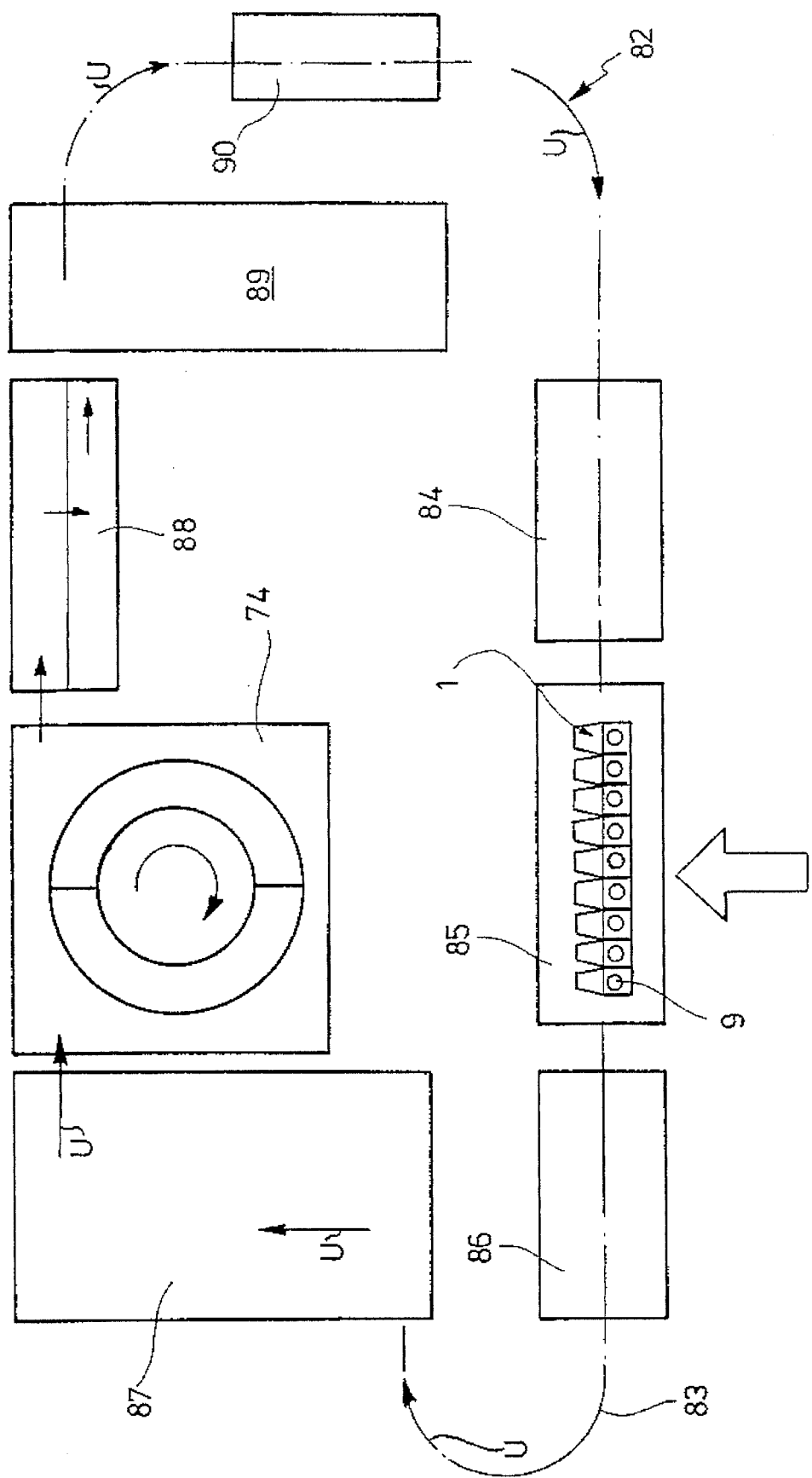

5,538,493

CENTRIFUGATION SYSTEM WITH A ROTATABLE MULTI-ELEMENT CARRIER

BACKGROUND OF THE INVENTION

The subject matter of the invention relates to a system or device for the centrifugation of samples comprising a rotor and at least one carrier having several uptakes for samples.

Dosing, mixing, tempering, filtering, closing, opening, washing, numbering, coding, retrieving, arranging and centrifuging are typical procedures when treating samples in laboratories. People endeavor to expedite those procedures by means of a convenient sample organization. Furthermore, they strive for a best possible automatization of the treatment of samples.

To achieve a common handling of the sample receptacles, there are already known chain-like systems using uptaking cylindrical receptacles. The uptaking cylinders are connected to each other by means of axially parallel swivelling joints allowing a chain-like movement around narrow radii, for instance in analyses devices. It's true that the chain simplifies the laboratory organization by facilitating the transportation, numbering, coding and retrieving of laboratory receptacles. However, charging of the receptacles presents a problem and in most cases, makes numerous manual sorting procedures indispensable. As to sample receptacles using a conventional sealing, the centrifugation makes an inclined or horizontal arrangement of the axis of a receptacle on the rotor necessary, which arrangement impairs the mass balance and may result in undesirable intermixtures after taking samples away and putting the chain upright again.

In principle, the sample receptacles may have a horizontal, inclined or vertical arrangement during centrifugation. There also do exist centrifuges with rotors using a swivel arm controlled by centrifugal force, so that the receptacles are vertically aligned as soon as the centrifuge stops, while they show an inclined or nearly horizontal alignment during centrifugation. In biochemical laboratories and in the microbiological field there are preferred rigid rotors where the laboratory receptacles are arranged at a slant angle of 45°. On the one hand, the position of the samples in the centrifuge is of significance since the maximum way of sedimentation—which has an influence on the time of centrifugation and causes the precipitate to separate from the liquid as a result of the difference in density—depends thereon. A horizontal alignment of receptacles entails a maximum way of sedimentation, while a vertical alignment entails a minimum way of sedimentation. On the other hand, it proves to be relevant with respect to the accelerations during the centrifugation procedure, which accelerations, typically, may be equal to 15000 times the acceleration of earth. The cover seal is strained least by the sample when the receptacle is horizontally aligned and is strained most when it is vertically aligned. An inclined alignment of the receptacle might be a good compromise.

Up to now, laboratory centrifuges either had been charged manually or automatically by means of a special laboratory robot. It also became public knowledge to pre-charge the rotor manually or automatically and to connect it to the centrifuge thereafter. A partial charging, however, makes a symmetric mass distribution on the rotor necessary. These procedures are very troublesome and imperfect when choosing the manual way of operation and very time-consuming when preferring the automatization. An automatization of the centrifugation by simultaneously speeding up the procedure would be especially desirable with respect to repeated centrifugations without exchanging receptacles within one procedure. This, above all, is the case in the molecular biological field, for instance, when obtaining DNA from plasmids or bacteriophages. A periodic change between the dosing, mixing, centrifuging and tempering stations is characteristic for such a process.

Taking all this into consideration, the invention is based on the subject to produce a system for centrifugation favoring the treatment of samples in the laboratory field as well as the automatization thereof.

SUMMARY OF THE INVENTION

These and other objects of the invention, which will become apparent hereinafter, are achieved by arranging the uptake elements of the carrier on a circle having its center lying on the rotational axis of the rotor.

Regarding the system according to the invention, the carrier allows to uniformly uptake, transport and treat a plurality of samples. This helps to reduce the number of transmission steps of the sample receptacles as well as the expenditure of time and handling resulting therefrom. So, for example, it is not necessary to change position of individual receptacles when passing over from a mixing station to a centrifuge. On the other hand, it is particularly easy to put the carriers in their bent position on the rotor while containing a plurality of samples. Furthermore, in consideration of the fact that the sample receptacles are arranged on a circle having its center point on the rotational axis of the rotor. The centrifugation itself is influenced positively, especially in regard to the mass balance and an optimum alignment of the samples towards the axis of the centrifuge.

In case a treatment of the samples outside the rotor is desired, the elements and uptakes thereof can be turned into a linear position, i.e. on a straight line. This alignment is to be preferred for other procedures, such as for charging, removing, opening and closing receptacles, adding, diluting and removing as well as transferring samples. The carriers, if necessary, can be automatically handled block by block then. A symmetry of the rotor charge is guaranteed by a uniform arrangement of the same number of receptacles on all carriers of the rotor. The system according to the invention, for the first time, allows an automated run of the centrifugation procedure by, at the same time, including it in an automatic treatment of samples by collecting said samples block by block and optimally aligning them within and/or outside the rotor without changing the carrier of the receptacle.

The alignment of the sample receptacles outside the rotor, preferably, is vertical. Whenever the uptakes for the sample receptacles are arranged parallel to the joint axes of the carrier, the samples are arranged vertically inside the rotor, too. For an inclined arrangement of the samples within and, if necessary, outside the rotor, the uptakes can be inclined towards the swivel axes. In this way, satisfactory centrifugation terms can be realized and intermixing effects are avoided. To avoid unfavourable strains of the covers of the sample receptacles, the uptakes with their charging holes can be closest to the center of the circle when being arranged on a circular path. The sample receptacles, however, can be alignable towards the vertical at a first angle outside the rotor, too, and can be alignable at a second angle outside as well as inside the rotor.

To align the sample receptacles towards the vertical at certain angles, the elements can have first and second alignment faces. Those alignment faces can be contact surfaces supporting said elements. However, there also can be concerned lateral faces where said elements can be secured to.

The chain-like arranged elements of the carrier with all uptakes on a circular path can be turned from a bent position into a position limited by external stops, where all uptakes are arranged on a straight line then. Consequently, the samples in the uptakes are arranged on a circular path when being in the bent position and are arranged on a straight line when being in the linear position. In addition, the carriers can have internal stops preventing the elements from making another swinging movement away from the straight line. "Outer stops" are provided outside with respect to a circle through the uptaking centers in a bent position, while "inner stops" are provided inside with respect to a circle.

Besides, the elements of the carrier can have parallely arranged first and second bearing surfaces extending in the same direction as the uptakes allowing adjacent carriers to connect thereto. Furthermore, to allow a space-saving arrangement and mutual support of various carriers, the elements can be provided with complementarily formed projections and recesses.

The carriers can serve the purpose of uptaking sample receptacles, including centrifuge tubes or glasses. For this purpose, the uptakes, at least certain parts thereof, can be adapted to the external contour of sample receptacles. The uptakes can be shorter than the sample receptacles to be inserted, so that, e.g. for mixing and tempering purposes, said receptacles are influenceable from outside from below and above. If the uptakes are completely surrounding the receptacles to be inserted on the side opposite to the cover, said receptacles are prevented from getting deformed in consequence of high centrifugal forces. Furthermore, the uptakes can be closed below their charging holes for a direct uptaking of samples. The elements will be provided with covers for the receptacles then. To allow an optic measurement and judgement of the receptacles and the contents thereof, the elements, at least partially, can be transparent.

The elements of the carrier can be shaped like blocks, while the holes the blocks are provided with do represent the uptakes. However, to save material, the elements can also be shaped like plates and be provided with uptakes shaped like tubes. The plate-like elements are connected to each other at their lateral edges. Said tubes are arranged at a certain angle towards the plate-like elements.

The joints can be worked as strap hinges either provided additionally or as one piece together with the elements or as additional joining elements using anchorages for the joint uptakes of the elements. Besides, combinations of pegs and peg uptakes can be taken into consideration for adjacent elements.

Preferably, the carriers are provided with means for stabilizing the elements in the bent and/or the linear position which can use elastically mounted elements, lock or magnets being efficient in the final positions.

Furthermore, the carriers can have means for connecting them to the rotor or transportation facilities which, preferably, move into engagement on a special joint level and are provided with positively locking or frictionally engaged means or magnetic means. To allow a stabilization of the position, a radial arm of the rotor can move into engagement between the ends of the carrier each time. Said radial arm can use coupling means in addition to those of the carrier.

Each carrier in a bent position, preferably, covers one segment of the circle only. One rotor is equipped with several carriers then always, which procedure, as a result of a symmetric arrangement of the gap between the carriers, leads to a satisfactory distribution of mass.

The carrier elements, preferably, are made of plastics and/or metal. In general, a resistant and solid material will be chosen.

The rotor can use one contact surface for at least one carrier in a bent position and at least one radial support for that carrier. The radial support can be provided inside and/or outside.

The transfer of said carrier to the rotor or away from the rotor can be made along axial, radial and/or tangential guides. Outside the rotor the carriers can be arranged in a linear position, parallely and/or serially to each other.

Preferably, each carrier passes a moving path where, besides other treatment equipment, a centrifuge can be provided. Irrespective of the design of said moving path, it can use a dosing station, mixing means, tempering means, a cover closing station or cover opening station.

The movement of the carrier along a path can be controlled by an automatic control system, preferably, a program control which can control the carrier transportation as well as the procedures in the treatment stations on the moving path. There can be realized different procedures for different carriers or groups of carriers, too.

BRIEF DESCRIPTION OF THE DRAWINGS

Further details and advantages of the invention result from the following description of the drawings demonstrating preferred embodiments. The drawings show the following:

FIG. 3 is a cross-sectional view of a carrier element with the uptake thereof inclined to a vertical at an angle of 450;

FIG. 4 is a top view of the carrier, an element of which shown in FIG. 3, with the carrier elements in a linear position;

FIG. 5 is a cross sectional view of a carrier element with the uptake thereof inclined towards the joint axis at 45° with first, second and third surfaces.

FIG. 6 is a top view of the carrier element shown in FIG. 5;

FIG. 12 is a view showing connection of a carrier with a rotor;

FIG. 13 is a partial top view showing magnetic means for connecting a carrier to a rotor;

FIG. 14 is a cross-sectional view showing mounting on a rotor of a carrier with a sample receptacle received in the uptake of a carrier element;

FIG. 15 is a cross-sectional view showing a different arrangement of a sample receptacle in the uptake of a carrier element;

FIG. 16 is a view showing a carrier inside cover opening means;

FIG. 17 is a view showing a carrier inside cover closing means;

FIG. 18 is a view showing a carrier, with openings provided across the uptake, inside an optic measuring facility;

FIG. 19 is a front view of a one-piece carrier molded of a plastic material;

FIG. 20 is a top view of a carrier shown in FIG. 19;

FIG. 21 is a side view of a carrier element with a sample receptacle molded integrally therewith;

FIG. 22 is a top view of an automatic centrifuge with a tangential rotor charge and separate input and output stations;

FIG. 23 is a schematic top view of automatic analyses means with a closed moving path for the carrier and with a centrifuge arranged in the moving path;

DETAILED DESCRIPTION OF THE PREFERRED EMBODIMENTS

In the following descriptions of various examples functionally identical or similar construction elements are provided with identical reference numbers.

Figure 1:
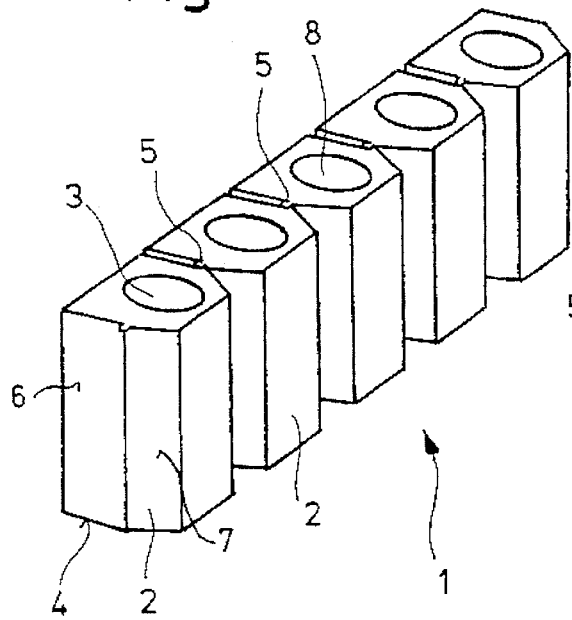
FIG. 1 is a perspective view of a carrier of a system for centrifugation of sample according to the present invention, with carrier elements being arranged along a straight line and parallel to each other.
Figure 2:
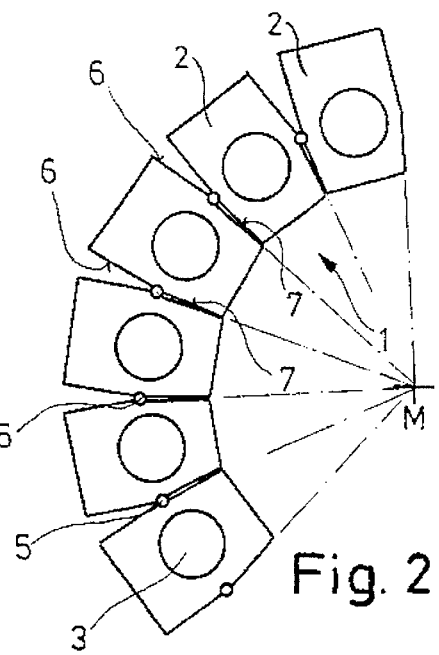
FIG. 2 is a top view of the carrier shown in FIG. 1 with the carrier element arranged along a circle.

A carrier 1 according to FIG. 1 and 2 has several elements 2 which use one uptake 3 each. Said uptakes are supported by first contact surfaces 4 in the linear position according to FIG. 1 as well as in the bent position according to FIG. 2.

Between the elements 2 joints 5 are provided, the axes of which are arranged parallely to uptakes 3 and vertically to said first contact surfaces 4. Besides, each element 2 has outer lateral faces 6 which are arranged parallel to uptakes 3 and vertically to said first contact surfaces 4, too. The outer lateral faces 6 act as stops which meet between the elements when carrier 1 is in a linear position. On the opposite side of joints 5 inner lateral faces 7 are provided which are also arranged parallel to uptakes 3 and vertically to said first contact surface 4 and diverge in each element towards joints 5. The inner lateral faces 7 also act as stops which meet between adjacent elements 2 while carrier 1 is in a bent position.

In said carrier 1, the sample receptacles inserted by upper charging holes 8 of elements 2 are vertically arranged in the linear as well as in the bent position of carrier 1.

A carrier 1 according to FIG. 3 and 4 differs from that carrier according to FIG. 1 and 2 by the fact that uptakes 3 are inclined towards the axes of joints 5 at 45° and, consequently, are inclined towards the first contact surface 4 at 45°, too. Also in this case the slewing capacity of elements 2 is limited by outer lateral faces 6 for the linear position and inner lateral faces 7 for the bent position (not shown). Thus, a sample receptacle 9 inserted by charging hole 8 is inclined towards the vertical at 45° in both final positions of carrier 1. Consequently, the seal provided by means of a receptacle cover 10 is only slightly strained by centrifugal forces. An exact alignment of sample receptacles 9 in carrier 1 is reached by two guides 11 spaced apart from each other and allowing a guiding of cover 10 on both sides.

Elements 2 of a carrier according to FIG. 5 and 6 use first contact surfaces 4 arranged vertically to their uptakes 3. Second contact surfaces 12 supporting element 2 are arranged towards said first contact surfaces 4 at an inclination of 45°. Thus, the sample receptacles inserted into uptakes 3 of elements 2 by means of a charging hole 8 are arranged vertically, while the carrier is supported by said first contact surfaces 4. They are inclined towards the vertical at 45°, while the carrier is supported by said second contact surfaces 12. In the linear position, the carrier, preferably, is supported by said first contact surfaces 4, whereas, in the bent position, it needs to be supported by said second contact surfaces 12.

Limitations of the pivoting angle are provided by means of outer lateral faces 6 on the one side of joints 5 also arranged parallel to each other and by means of inner lateral faces 7 on the other side of said joints being at an angle with each other. The outer lateral faces 6 act as stops for the linear position, while the inner lateral faces 7 act as stop faces for the bent position of the carrier.

To stabilize the position of the carrier in the final positions, each element 2 uses permanent magnets 13 in the outer and inner lateral faces which can have a tight fit in said lateral faces. The permanent magnets 13 are acting together with corresponding magnets of an adjacent element 2 with the effect that magnets in the outer lateral faces 6 are attracted to each other while being in the linear position and magnets in the inner lateral faces 7 are attracted to each other while being in the bent position to keep the carrier in the momentary position.

In the lower portion of elements 2, the inner lateral surfaces 7 adjoin wall sections 14 which are spaced apart from each other and, to stabilize position, can uptake corresponding charging elements of other components of the system.

Joints 5 are worked as strap hinges which are kept in upper and lower grooves 15 of elements 2 and connect to each other all elements of the carrier.

Elements 2 have a third contact surface 16 which is aligned parallel to the uptake 3 as well as the first contact surface 4. Said third contact surface 16 can serve for the horizontal storage of samples in the linearly aligned carrier.

If elements 2 are supported by the first contact surfaces 4, any inserted sample receptacles 9 are aligned vertically. This arrangement is preferred in the linear position of the carrier. In the linear position as well as in the bent position of the carrier, the elements 2 can be supported by the second contact surface 12 which is aligned vertically to the joint axes. The sample receptacles 9 then are inclined towards the vertical at 45°. Finally, in the linear position of the carrier, the elements 2 can be supported by the third contact surfaces 16. In this case, the sample receptacles are aligned horizontally.

Figure 7:
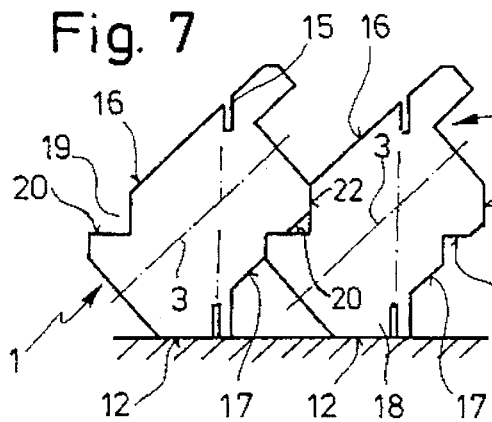
FIG. 7 is a side view of two carrier elements of another embodiment of a carrier in an inclined position of the carrier elements.
Figure 8:
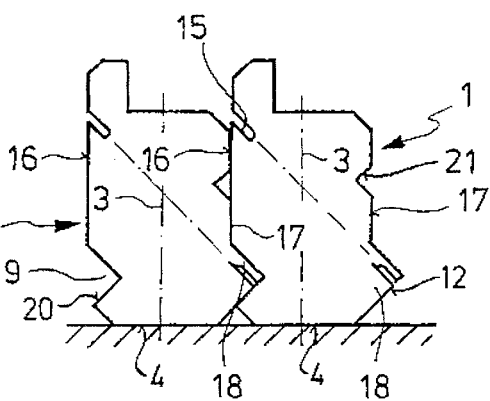
FIG. 8 is a side view of the carrier elements shown in FIG. 7 in an upright position of the carrier elements.

Said third contact surface 16, at the same time, is a first bearing surface which goes into effect when adjacent carriers move into one another. As FIG. 7 and 8 show, on the opposite side of uptake 3, a second bearing surface 17 is arranged parallel to the first bearing surface 16. Said second bearing surface 17 is provided with a projection 18 within reach of the second contact surface 12, while the first bearing surface 16 is provided with a complementary recess 19 there. FIG. 8 shows that, in the linear position, adjacent carriers 1 supported by their first contact surfaces 4 can move against each other with their first and second bearing surfaces 16, 17 and, in this way, can move into one another with their projections 18 and recesses 19. Consequently, in spite of the second contact surfaces 12, a space-saving storage of parallel carriers 1 can be realized.

Recess 19 as well as the first contact surface 4 delimit outside steps 20 of each element of carriers 1 at the side of the first bearing surface 16. In the second bearing surfaces 17, however, there are provided inner steps 21 which meet the outer steps 20 of carriers 1 supported by the second contact surfaces 12 and, in this way, cause a mutual support as well as saving of the store room (FIG. 7). Besides, each second bearing surface 17, in its upper portion, has an inclination 22 which, when the carrier is in an inclined position, puts against a wall of recess 19 and provides an additional support.

These carriers 1 also have outer and inner lateral faces 7, 8 which, in a linear and bent alignment, act as stops.

Figure 9:
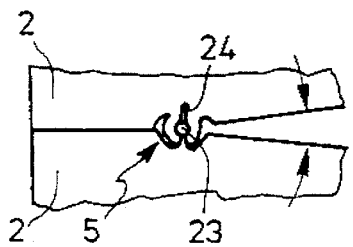
FIG. 9 is a partial longitudinal view of two carrier elements connected by an articulated joint.

As shown in FIG. 5 to 8, there are provided upper and lower grooves 15 which serve the uptaking of strap hinges for forming a joint. According to FIG. 9, adjacent elements 2 of a carrier can also be linked by means of molded joining elements, a first one of which uses a pin 23 connected with the element by a link and a second one of which is provided with means 24 for uptaking said pin using a feedthrough slot for said link connection.

Figure 10:
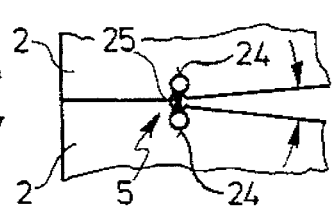
FIG. 10 is a view similar to that of FIG. 9 showing another type of an articulated joint for connecting two carrier elements.
Figure 11:
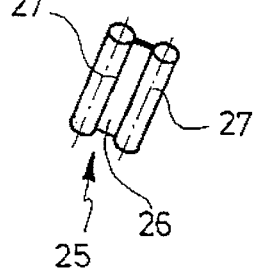
FIG. 11 is a perspective view of an articulated joint shown in FIG. 10.

According to another alternative according to FIG. 10 and 11, a joint 5 can be provided with an additional joining element 25 using a central link 26 and connecting pins 27 at both sides. Said connecting pins 27 are inserted into pin uptakes 24 of two adjacent elements 2 using feedthrough slots for the central link 26.

FIG. 12 shows a carrier I according to FIG. 7 and 8 which, with its second contact surface 12, is supported by a lower marginal flange 28 of a rotor plate 29, while carrier 1, with it second bearing surface 17 and the upper part of its projection 18, is supported against a complementarily formed core 30 of the rotor plate 29.

Said figure also shows said carrier 1 in a adjacent position on a delivery line 31 allowing said carrier 1 to be tilted back in the direction of delivery.

To secure carrier 1 to the rotor 29, however, there, on the second contact surface 12, at least of an outer carrier element 2, there are provided coupling means 32 which can be a permanent magnet, too. Said coupling means 32 can also serve for the coupling of a transportation equipment (chain, band) and are arranged exactly on the same level as joints 5.

According to FIG. 13, said carrier 1, on the inner lateral face 7 of an outer element 2, is additionally provided with a metal plate 33 which acts together with a magnet 34 of a radial link 35 of the rotor 29. The other outer element 2 (not shown) of carrier 1 is provided with a magnet 34 which acts together with a metal surface in a radial link of the rotor 29.

Taking a carrier 1 with elements 2 according to FIG. 5 and 6 as a basis, FIG. 14 and 15 show further details of the system inside and outside the rotor 21. According to FIG. 20, the carrier 1, with its second contact surfaces 12, is supported on the rotor plate 29 in a bent position and is supported radially by the core 30 of the rotor inside, while an inserted sample receptacle 9, with an edge above cover 10, is supported by the upper part of carrier 1 and a bottom portion thereof projects from an opening 38 at the bottom.

Besides, the rotor 29 has a rotor cap 39 which can be moved into an unlocking position—shown while extended—and into a locking position—dashed line—in an axial moving direction V. The rotor cap 39 embraces the carrier 1 while being in the locking position and supports it radially on the third contact surface 16 from outside.

FIG. 15 shows the same carrier 1 supported by its first contact surface 4, while a base 40 acts on the bottom portion of the sample receptacle 9 and lifts it in the lifting direction H, so that its cover 10 removes from the upper portion of said carrier. In this way, said receptacle 9 can be easier accessed. Said sample receptacle, preferably, is aligned vertically then.

The carrier 1 according to FIG. 7 and 8 as well as FIG. 12, 13, is shown, in FIG. 16, inside means 42 for opening the cover. There is provided a base plate 43 using securing strips 44, 45 which take hold of carrier 1, which is supported by its first contact surface 4, which is its projection 18 and its gap 19. The carrier 1, with its guides 11, is pushed under holding-down means 46 which are firmly connected with the base plate 43.

As shown in FIG. 15, inserted sample receptacles 9, with the edge of their cover 10, project from an upper supporting portion of said carrier 1.

Furthermore, the base plate 43 connects to guides 47 using forks 48 movable in direction R. Said forks 48 take hold of one cover 10 each time and open it in upward direction while moving. Said holding-down means 46, meanwhile, are holding each receptacle at a point where the hinge fitting of the cover is provided, which step prevents the fork 48 from pulling said receptacle out of the carrier 1. Those holding-down means 46 can be replaced by a radial load of receptacle 9 to secure the same.

The cover closing means 49 according to FIG. 17 also use a base plate 43 as well as lateral securing strips 44, 45 acting together with projection 18 and uptake 19 of a carrier 1. Compared to means 42, the securing strip 44 of means 49 has got a slightly higher position, so that it is laterally supporting the carrier 1 by the second bearing surface 17.

Considering the fact that the carrier 1 is supported by the base plate 43, the inserted sample receptacles 9 are slightly lifted, while an opened cover 10 projects from the guides 11. A pressure roller 50 can be moved towards the base plate 43 in parallel direction P, so that, when acting on cover 10, puts it together with the main portion of the sample receptacle 9 by swinging movements, closes and locks it.

FIG. 18 shows a carrier which is similar to that according to FIG. 7 and 8 as well as 12, 13, however, is additionally provided with openings 51 across the uptake 3 containing a sample receptacle 9. Also in this case the carrier 1, with its first contact surface 4, is supported by a base plate 43, so that the sample receptacle is slightly pushed out.

The opening 51 serves for the optic control of the contents of the receptacle. For this purpose, a photometric device 52 using a light transmitter 53 and a receiver 54 is aligned with the axis of said opening 51.

FIG. 19 and 20 show another carrier 1 which is molded of plastics as one piece. Its elements 2 have uptakes 3 which are vertically aligned towards a first contact surface. A second contact surface 12 is provided at an angle of 45° therewith. The axes of joints 5 are arranged parallely to the second contact surface 12 and, consequently, are aligned at an angle of 45° with the uptakes 3.

The elements 2 of said carrier have inner and outer lateral faces 36 for limiting the pivoting angle. FIG. 20 shows that, in a linear position, the outer lateral faces 6 are somewhat spaced apart from each other, so that the elements can be arranged at a slight angle with each other.

Joints 5 are formed as strap hinges and, at the side facing the inner lateral faces, have a radius which facilitates a tilt into the bent position, however, counteracts a tilt beyond the linear position. Joint 5 so far takes part in the limitation of the pivoting angle.

According to FIG. 21, a carrier 1 molded of plastics as one piece, can form a receptacle with its uptakes 3 for uptaking samples directly. Uptake 3 is closed in downward direction towards the first contact surface 4 and can be closed by a cover 10 above which is linked by means of a strap hinge. Furthermore, there is provided a second contact surface 12 for a sample arrangement made diagonally to the centrifuge axis. The axes of joints 5 for connecting separate elements of this one-piece carrier 1 cross the intersection line of the first and second contact surfaces 4, 12.

FIG. 22 shows the basic structure of an automatic laboratory centrifuge 74. The rotor 29 is provided inside a central area behind a control panel 77. On the one side of said central area there is arranged an input station 78, while on the other side, an output station 79 is provided. A guide rail 80 runs from the input station 78 to the output station 79 and passes said rotor 29 tangentially.

At the input station there are arranged several rows of carrier 1 which are actuated towards the input arrow E. These are carriers which were described with reference to FIG. 7, 8, 12, 13.

Just before reaching the guide rail 80, each carrier 1 is tilted from the first contact surface 4 to the second contact surface 12 by means of suitable facilities. It then is pushed on guide rail 80 and passed on to rotor 29. According to FIG. 22, said rotor 29 is so constructed that it can take two carriers 1 between two radial links 25. Said rotor 29 has a rotor cap which, to radially lock or unlock carrier 1, is axially movable.

Further facilities not shown here cause the carrier 1 to return from rotor 29 to guide rail 80 after the centrifugation of the samples. Said guide rails takes them to the output station 79, where they are transported in the direction arrow A. While changing from the guide rail 80 to the output station 79 another mechanism causes the carriers 1 to tilt from their tilted position on the second contact surface 12 back to their original position on the first contact surface 4 with vertically arranged receptacles. The change of position is symbolized in FIG. 22 at the outer edge of the output station 79.

FIG. 23 shows an automatic centrifuge 74 integrated into automatic anylyses facilities 82 which the carriers 1 pass through on a closed curved park 83.

The carriers 1 are charged with new sample receptacles 10 by means of charging facilities 84. Subordinate to said charging facilities there are arranged supply means 85 in circulation direction U of carriers 1 for delivering, dosing or diluting samples. The covers of the sample receptacles are closed there, too.

Said supply means are followed by mixing facilities 86 also arranged in circulation direction U and supplying carriers 1 to storing and tempering facilities 87.

After a certain residence time in said storing and tempering facilities 87 the carriers 1 reach the centrifuge 74. After termination of the centrifugation there are passed decanting facilities 88 which are followed by measuring facilities 89. Thereafter, the carriers 1 are passed on to output facilities 90, where the sample receptacles 9 are removed and passed over in a suitable manner.

Figure 24:
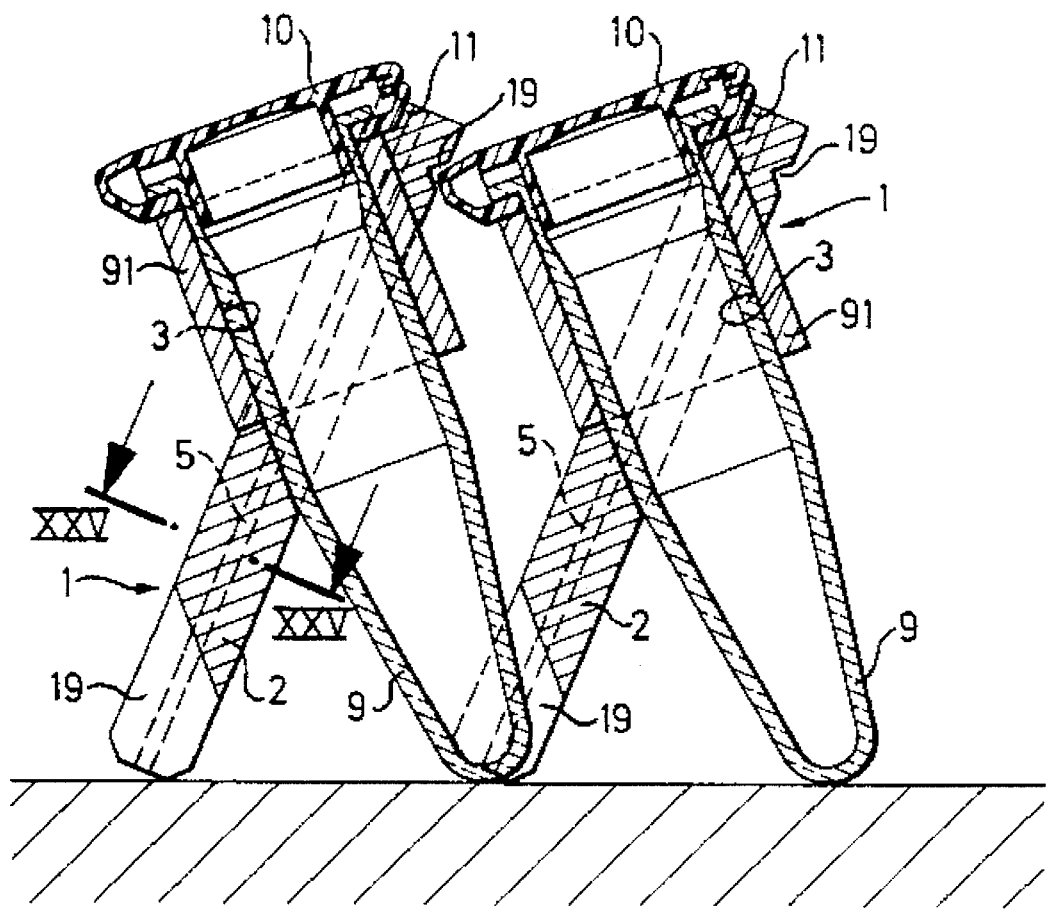
FIG. 24 is a cross-sectional view of a portion of a carrier with peale-like carrier elements with sample receptacles located in the carrier elements.
Figure 25:
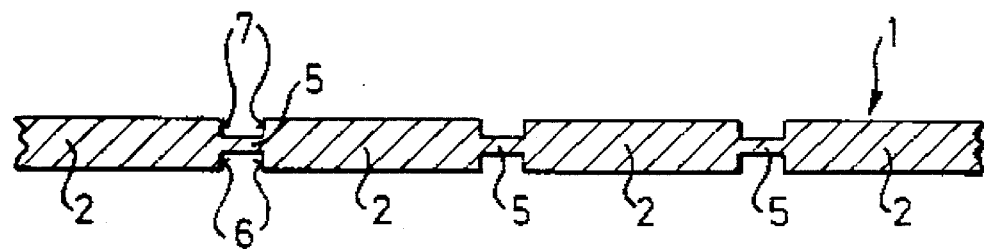
FIG. 25 is a cross-sectional view along line 25–25 in FIG. 24.

Carriers according to FIG. 24 and 25 have plate-like elements 2 linked at their lateral edges by means of joints 5 formed as strap hinges. Like the form of construction according to FIG. 19 and 20 said joints 5 allow the elements 2—starting from the linear position of carrier 1—to turn in both directions. The slewing capacity, however, is limited by means of inner and outer lateral faces of carrier 1.

Each element 2 is provided with a tube 91 which is aligned at an acute angle with the plate and, accordingly, with the axes of joints 5. Said tubes 91 surround uptake 3 crossing elements 2.

According to FIG. 24, the uptakes 3 contain, frictionally engaged, sample receptacles 9. Said sample receptacles 9, near their cover portion, are taken between guides 11 of the plate-like base components of elements 2. Besides, the lateral portions of covers 10 are supported by the upper faces of the tubes 91. The elements 2 as well as the sample receptacles 9, with their bottom portions, are supported on a base defining a contact surface. According to the drawn position outside the rotor, the sample receptacles 9 are aligned at a relatively small angle with the vertical. This causes a satisfactory CG position for stability.

To additionally improve the stability and space-saving arrangement, the sample receptacles 9, with another lateral portion of their covers 10, are taken by a gap 19 in the upper portion of an adjacent element 2. The bottom portions of sample receptacles 9 use projections engaging with gaps 19 in the lower portion of an adjacent element 2.

Figure 26:
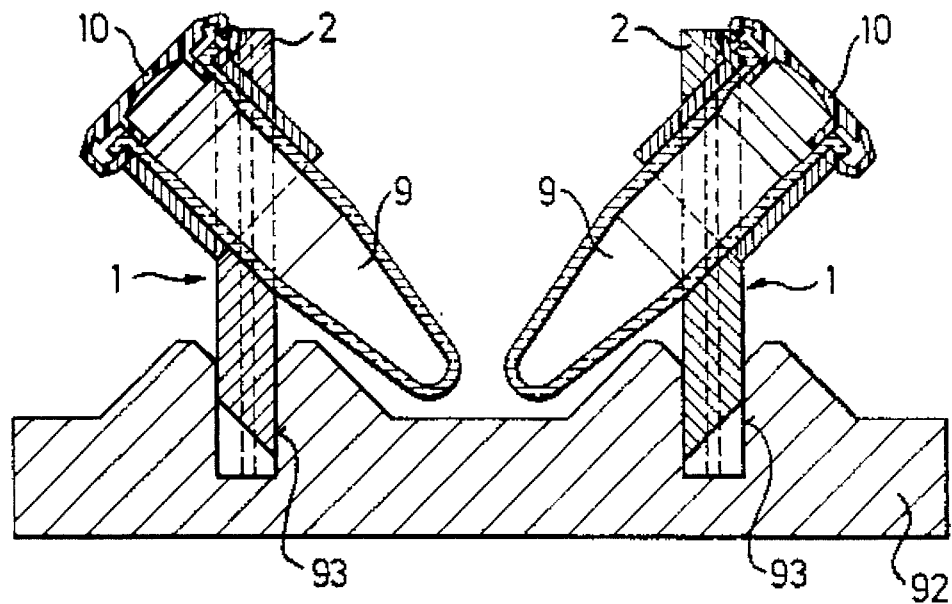
FIG. 26 is a view of an arrangement of two carrier elements on a work desk.
Figure 27:
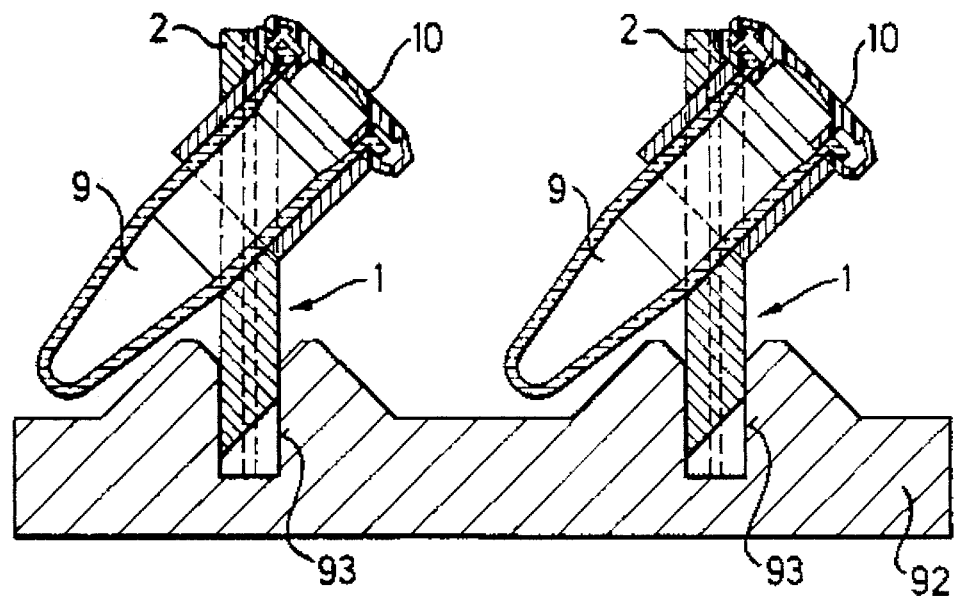
FIG. 27 is a view of an another arrangement of two carrier elements on a work desk than that in FIG. 26.

According to FIG. 26 and 27, there can be provided a work desk 92 for positioning the before-explained carriers 1 outside a rotor. Said work desk 92 uses parallel insert grooves 92 for opening connection to lower portions of the plate-like elements 2. Carriers 1 are kept in their grooves 93 frictionally engaged, so that a handling is possible while exerting on sample receptacles 9 an influence of force, e.g. while inserting or removing or opening or closing the covers According to FIG. 26, the carriers are so aligned that the sample receptacles 9 hardly restrict an access to the upper portion of carrier 1. The alignment of said sample receptacles 9 according to FIG. 27 allows inserting or taking samples in the same direction. In both cases, the sample receptacles 9 are more inclined towards the vertical than FIG. 24 shows, which fact makes an access from aside easier.

Figure 28:
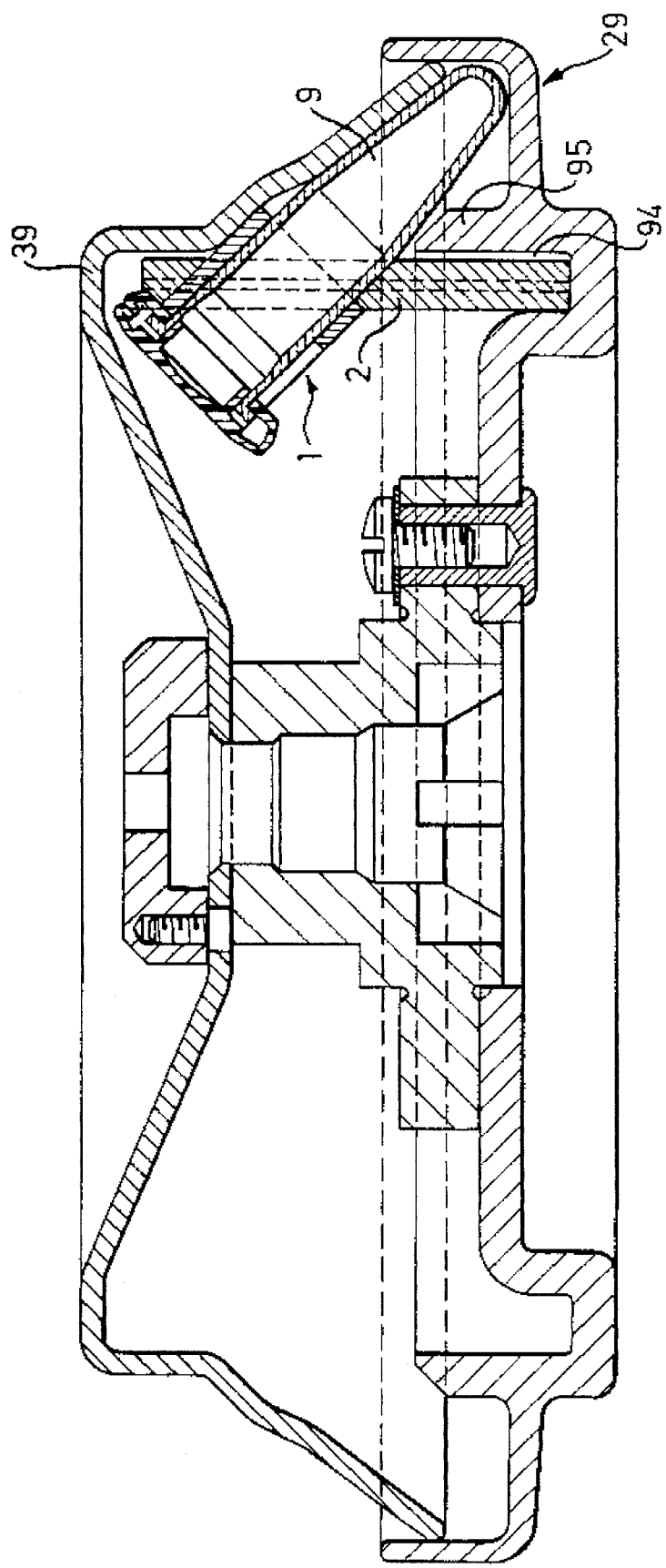
FIG. 28 is a cross-sectional view of a carrier of FIGS. 26 and 27 supported on a rotor.

A carrier is designed for six sample receptacles 9, so that several carriers are to be arranged on a rotor 29 according to FIG. 28. Said rotor 29 uses a circular groove 94 for opening a connection to the lower portions of the plate-like elements 2. Groove 94 has a higher groove wall radially outside than radially inside for largely supporting the carrier 1 towards any effects by centrifugal forces. In the upper portion of their elements the carriers 1 are supported by a rotor cap 39, while receptacles 9, with their bottom portions, are supporting against said rotor cap 39, too.

Figure 29:
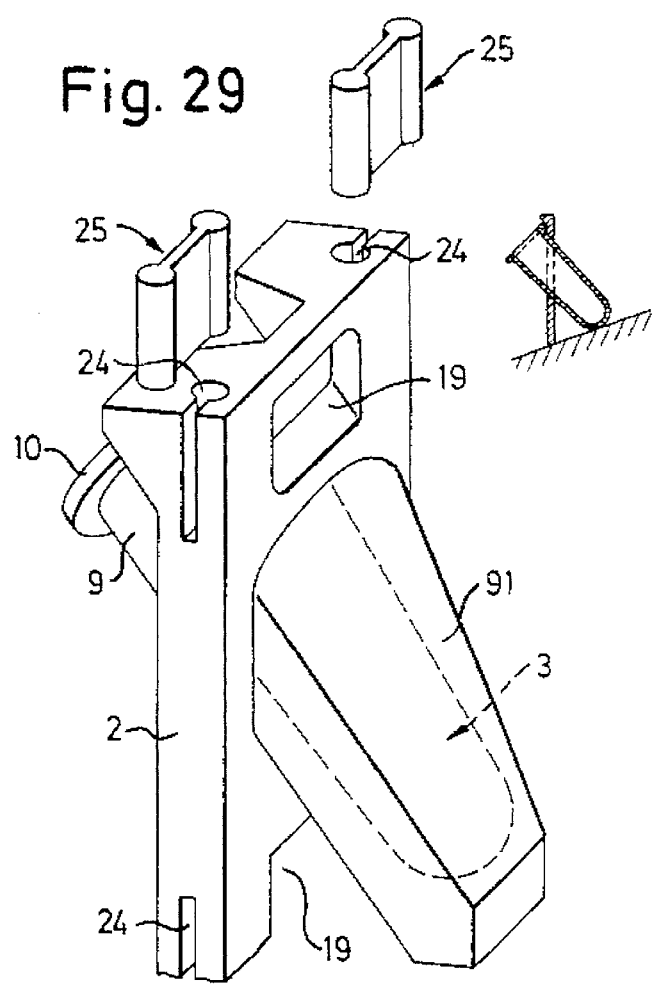
FIG. 29 is a perspective view of an embodiment of carrier element according to the invention.

Carrier 1 explained before can be molded of plastics as one piece. As a result of the short tubes 91 which cover the sample receptacles 9 partly only, the contents of said receptacles can be easily controlled. The carrier according to FIG. 29 explained in the following allows a control of the receptacle in as a result of its transparent design. Its elements 2 are connected with each other by means of joining elements 25 shown by FIG. 11.

The transparent elements 2 also use a plate-like base component which, in its lateral portion, shows pin slots 24 above and below for opening a connection to elements 25. Each of the plate-like base components is also connected with one tube 91 which, on the front side of elements 2, as shown, is completely closed. Tube 91, thus, is used as an uptake 3 which completely surrounds an inserted sample receptacle 9 on the side opposite to cover 10. In their upper and lower portions said plate-like elements 2, in return, are provided with openings 19 for the cover portion of the adjacent receptacle 9 or the bottom portion of an adjacent tube 91. In this way, a mutual support of adjacent carriers, similar to that shown by FIG. 24, can be realized. The sample receptacles, in that case, are aligned at a first angle towards the vertical.

Figure 30:
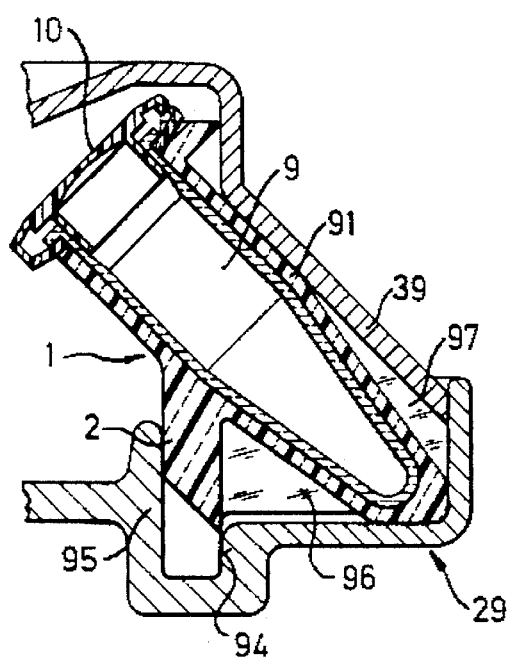
FIG. 30 is a cross-sectional view of a carrier element shown in FIG. 29 supported in a rotor.
Figure 31:
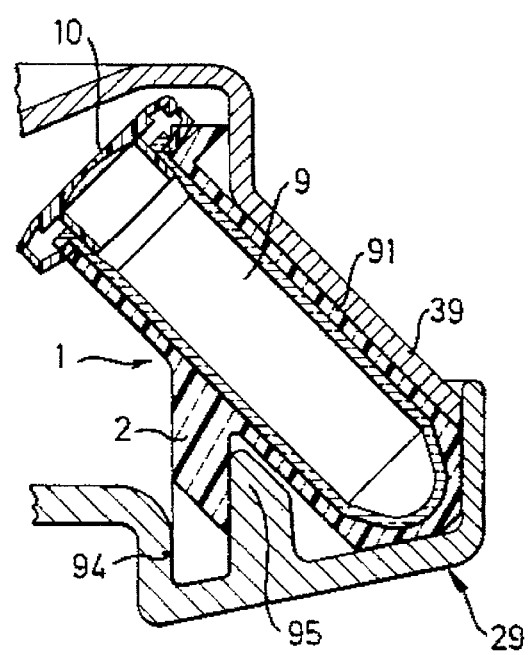
FIG. 31 is a cross-sectional view similar to that of FIG. 30 with another type of a rotor.

According to FIG. 30 and 31, the carriers 1, with the transparent elements 2, are inserted into different rotors 29 of centrifuges, while the receptacles 9 are aligned at a second angle towards the vertical which is higher than the first angle. The lower portions of the plate-like elements 2 are inserted into ring grooves 94 of rotors 29 which are vertically aligned.

According to FIG. 30, the ring groove 94, at its inner side, has a higher side wall 95 than outside allowing the carrier to connect from outside. There are provided additional ribs 96 between the plate-like element 2 and tube 91 as well as ribs 97 between tube 91 and rotor cap 39.

According to FIG. 31, the radial outer side wall 95 of the groove is higher allowing the carrier 1 to connect to the groove 94 from inside. As a result of the supporting effect of said outer side wall 95 any additional ribs are not necessary.

The carriers 1 explained before, for instance, accept sample receptacles for 0.5/1.5/2 mililitres.

What is claimed is:

1. A system for centrifugation of samples, comprising:
a carrier provided with a plurality of elements having each an uptake for receiving a sample to be centrifuged;
a rotor for supporting said carrier; and
joint means for connecting said plurality of elements with each other;
wherein said elements are arranged, in a centrifuged position of said carrier, along a circle, which has a center located on a rotational axis of said rotor;
wherein said elements have each first and second bearing surfaces for engaging respective bearing surfaces of the elements of adjacent carriers; and
wherein said first and second bearing surfaces are provided with complementary gaps and projections, respectively, for insuring a reliable connection of corresponding elements of the adjacent carriers.

2. A system for centrifugation of samples, comprising: a carrier provided with a plurality of elements having each an uptake for receiving a sample to be centrifuged;
a rotor for supporting said carrier; and
joint means for connecting said plurality of carriers with each other;
wherein said elements are arranged, in a centrifuged position of said carrier, along a circle, which has a center located on a rotational axis of said rotor; and
wherein said joint means comprises strap hinges for connecting the adjacent elements and joining elements each having two parts for anchoring in the adjacent elements.

3. A system for centrifugation of samples, comprising:
a carrier provided with a plurality of elements having each an uptake for receiving a sample to be centrifuged;
a rotor for supporting said carrier; and
joint means for connecting said plurality of elements with each other;
wherein said elements are arranged, in a centrifuged position of said carrier, along a circle, which has a center located on a rotational axis of said rotor; and
wherein said joint means comprises strap hinges for connecting adjacent elements.

4. A system according to claim 3, wherein said elements have first surfaces, to provide for vertical alignment of said elements, and second surfaces, which extend at an angle to said first surfaces to provide for alignment of said elements when they extend at an angle to a vertical.

5. A system according to claim 3, wherein said elements further have stop means for limiting a slewing movement of said elements relative to each other.

6. A system according to claim 3, wherein each uptake has an upper charging hole for receiving a sample receptacle, and guide means for guiding a cover of the sample receptacle to provide for substantially exact alignment of the sample receptacles in the carrier.

7. A system according to claim 6, wherein each uptake has a length, which is less than a length of the sample receptacle received therein, and a bottom opening through which a bottom end of the sample receptacle projects.

8. A system according to claim 6, wherein each uptake completely surrounds the sample receptacle received therein.

9. A system according to claim 3, wherein said elements have transparent portions for enabling optical control of the centrifuged samples.

10. A system according to claim 3, wherein said carrier is formed as a unitary block of said elements, and wherein said elements each have a hole defining an uptake.

11. A system according to claim 3, wherein said elements have a plate-like shape, and said uptakes are formed by tubes.

12. A system according to claim 3, wherein said joint means comprises joining elements each having two parts for anchoring in two adjacent two elements, respectively.

13. A system according to claim 3, wherein said carrier is formed as one piece.

14. A system according to claim 3, further comprising means for stabilizing said elements in a predetermined position thereof.

15. A system according to claim 3, wherein said system comprises means for connecting said carrier to said rotor.

16. A system according to claim 3, comprising a plurality of carriers uniformly distributed over an area of said rotor.

17. A system according to claims 3, wherein said rotor has a contact surface for supporting said carrier in the centrifuged position of said carrier, and at least one radial support for said carrier.

18. A system according to claim 3, comprising at least one of an axial guide, a radial guide, and a tangential guide for transferring said carrier relative to said rotor.

19. A system according to claim 3, comprising a plurality of carriers which are arranged, at least in one of storing, transporting and treatment positions thereof, along a straight line parallel to each other.

20. A system according to claim 3, comprising a plurality of carriers which are arranged, at least in one of storing, transporting and treatment position thereof, parallel to each other.

21. A system according to claim 3, further comprising means arranged in a moving path of said carrier for treating samples.

22. A system according to claim 3, further comprising cover closing means provided in a moving path of said carrier for sample receptacles received in the uptakes of said elements.

23. A system according to claim 3, wherein said elements, have:

first surfaces to provide for alignment of said elements at a first angle; and second surfaces to provide for alignment of said elements at a second angle.

24. A system according to claim 3, wherein said joint means comprises a plurality of joints having respective axes extending parallel to each other, and wherein said elements extend at an angle to the axes, and wherein said uptakes are located closest to the center of said circle in the angularly extending position of said elements.

* * * * *